United States Patent

Martinez-Lemus et al.

(10) Patent No.: US 11,684,603 B2
(45) Date of Patent: Jun. 27, 2023

(54) NEURAMINIDASE INHIBITION TO IMPROVE GLYCOCALYX VOLUME AND FUNCTION TO AMELIORATE CARDIOVASCULAR DISEASES IN PATHOLOGIES ASSOCIATED WITH GLYCOCALYX DAMAGE

(71) Applicant: The Curators Of The University Of Missouri, Columbia, MO (US)

(72) Inventors: Luis A. Martinez-Lemus, Columbia, MO (US); Christopher A. Foote, Columbia, MO (US); Jaume Padilla, Columbia, MO (US)

(73) Assignee: CURATORS OF THE UNIVERSITY OF MISSOURI UNIVERSITY, Columbia, MO (US)

( * ) Notice: Subject to any disclaimer, the term of this patent is extended or adjusted under 35 U.S.C. 154(b) by 414 days.

(21) Appl. No.: 16/754,814

(22) PCT Filed: Oct. 10, 2018

(86) PCT No.: PCT/US2018/055145
§ 371 (c)(1),
(2) Date: Apr. 9, 2020

(87) PCT Pub. No.: WO2019/075009
PCT Pub. Date: Apr. 18, 2019

(65) Prior Publication Data
US 2021/0186921 A1    Jun. 24, 2021

Related U.S. Application Data

(60) Provisional application No. 62/572,232, filed on Oct. 13, 2017.

(51) Int. Cl.
| | | |
|---|---|---|
| *A61K 31/351* | (2006.01) | |
| *A61K 31/215* | (2006.01) | |
| *A61K 31/445* | (2006.01) | |
| *A61K 38/47* | (2006.01) | |
| *A61K 31/196* | (2006.01) | |
| *A61P 3/10* | (2006.01) | |

(52) U.S. Cl.
CPC .......... *A61K 31/351* (2013.01); *A61K 31/196* (2013.01); *A61K 31/215* (2013.01); *A61K 31/445* (2013.01); *A61K 38/47* (2013.01); *A61P 3/10* (2018.01)

(58) Field of Classification Search
CPC .. A61K 31/351; A61K 31/196; A61K 31/215; A61K 31/445; A61K 38/47
USPC ...................................... 424/94.61
See application file for complete search history.

(56) References Cited

U.S. PATENT DOCUMENTS

2007/0270443 A1   11/2007   Went et al.

FOREIGN PATENT DOCUMENTS

CN   107812182 A   3/2018

OTHER PUBLICATIONS

Foote et al., Reversing glycocalyx degradation; identification of a pharmacological target to improve endothelial function in type II diabetes; The FASEB Journal, 2-pages, Abstract, 2017.

*Primary Examiner* — Kristin A Vajda
(74) *Attorney, Agent, or Firm* — Stinson LLP

(57) ABSTRACT

Disclosed are methods for ameliorating glycocalyx damage by administering a neuraminidase inhibitor. Also disclosed are methods for treating endothelial dysfunction and for improving flow mediated dilation.

15 Claims, 23 Drawing Sheets

NEURAMINIDASE INHIBITION TO IMPROVE GLYCOCALYX VOLUME AND FUNCTION TO AMELIORATE CARDIOVASCULAR DISEASES IN PATHOLOGIES ASSOCIATED WITH GLYCOCALYX DAMAGE

CROSS REFERENCE TO RELATED APPLICATIONS

This application claims priority to International Application No. PCT/US2018/055145, filed Oct. 10, 2018, which claims priority to U.S. Ser. No. 62/572,232, filed on Oct. 13, 2017, each of which is hereby incorporated by reference in its entirety.

STATEMENT OF GOVERNMENT SUPPORT

This invention was made with government support under HL-088105 and HL-107910 awarded by the National Institutes of Health. The government has certain rights in the invention.

BACKGROUND OF THE DISCLOSURE

The present disclosure relates generally to methods for treating cardiovascular disease. More particularly, the present disclosure is directed to methods for treating endothelial dysfunction. Also disclosed are methods for ameliorating glycocalyx degradation.

The glycocalyx is a thin layer of glycoproteins and proteoglycans interwoven with one another to form a luminal mesh that separates the endothelial cell membrane from the blood that flows within the vasculature. One of the primary functions of the glycocalyx is to serve as a mechano-transducer of shear stress. A second is to work as a semi-permeable barrier/sieve to the tangential flow of blood. In the vasculature, the generation of nitric oxide via flow induced dilation is mediated in part by the glycocalyx. Consequently, in pathologies in which the glycocalyx is compromised there is a concomitant reduction in the availability of nitric oxide. From a health perspective, this has significant implications. With respect to cardiovascular diseases, reduced bioavailability of nitric oxide is linked to increased platelet aggregation, vascular smooth muscle cell proliferation, leukocyte adhesion, LDL oxidation, neointima formation, modifications to the extracellular matrix and thrombosis. Thus, decreased availability of nitric oxide is posited to play a key role in the progression of atherosclerosis, arterial stiffening, and hypertension, pathologies which significantly increase the risk of coronary artery disease and other cardiovascular morbidities such as peripheral vascular disease and cerebrovascular disease.

Continuous exposure of the glycocalyx to shear stresses mediated by the flow of blood results in the constant shedding of its components, which are replaced via the biosynthesis of newly synthesized proteoglycans. The dynamic nature of the glycocalyx structure makes it quite sensitive to perturbations in vascular homeostasis, and thus relatively fragile. The glycocalyx is functionally compromised under conditions of inflammation, increased presence of reactive oxygen species, and hyperglycemia. In addition, a number of its constituent components such as sialic acids, hyaluronan and heparin sulfates are sensitive to enzymatic cleavage by neuraminidase, hyaluronidase and heparinase, respectively, leading to accelerated shedding, degradation and subsequent attenuation of flow mediated dilation (a proxy for nitric oxide production) and increased vascular permeability.

The Center for Disease Control reports that diabetes is currently the 7th leading cause of death in the United States. It is estimated that by 2050 as many as ¼ to ⅓ of adults in the United States could have diabetes. The health consequences from this disease are significant. Moreover, a large body of evidence indicates that diabetes is a major risk factor for cardiovascular disease, as it shows that more than 70% of patients with type 2 diabetes die from cardiovascular complications. In type 2 diabetes, endothelial dysfunction is consistently observed, as assessed by reduced nitric oxide bioavailability and/or increased vascular permeability. In addition, inflammation, reactive oxygen species and hyperglycemia are manifest and serum levels of the three major enzymes implicated in glycocalyx degradation (neuraminidase, hyaluronidase and heparinase) are increased.

There are few clinical studies evaluating the effectiveness of targeting the glycocalyx for restoration in patients with diabetes. In one study, administration of heparin sulphate (Sulodexide) in type 2 diabetic patients partially restored glycocalyx barrier function by decreasing vascular permeability, though endothelial release of nitric oxide was not assessed. In another study, short term statin treatment (Rosuvastatin) was used to treat patients with familial hypercholesterolemia. This approach was predicated on the hypothesis that oxidized lipids damage the glycocalyx via the generation of free radicals and by reducing the level of oxidized lipids, statin treatment could alleviate oxidant stress and glycocalyx damage. While statin treatment partially restored glycocalyx volume in patients with familial hypercholesterolemia, this coincided with an increase in plasma hyaluronidase activity, suggesting it is not an ideal treatment strategy for reversing glycocalyx damage, as hyaluronidase facilitates glycocalyx degradation. Accordingly, there exists a need for alternative treatment methods that target the glycocalyx for restoration.

BRIEF DESCRIPTION

In one aspect, the present disclosure is directed to a method for ameliorating glycocalyx damage in an individual in need thereof. The method includes: administering to the individual in need thereof a composition comprising a neuraminidase inhibitor.

In one aspect, the present disclosure is directed to a method for treating endothelial dysfunction in an individual in need thereof. The method includes: administering to the individual in need thereof a composition comprising a neuraminidase inhibitor.

In one aspect, the present disclosure is directed to a method for improving flow mediated dilation in an individual in need thereof. The method includes: administering to the individual in need thereof a composition comprising a neuraminidase inhibitor.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The disclosure will be better understood, and features, aspects and advantages other than those set forth above will become apparent when consideration is given to the following detailed description thereof. Such detailed description makes reference to the following drawings, wherein:

FIG. 6B is the same experimented with the x-axis plotted as wall shear stress.

DETAILED DESCRIPTION

Figure 1:
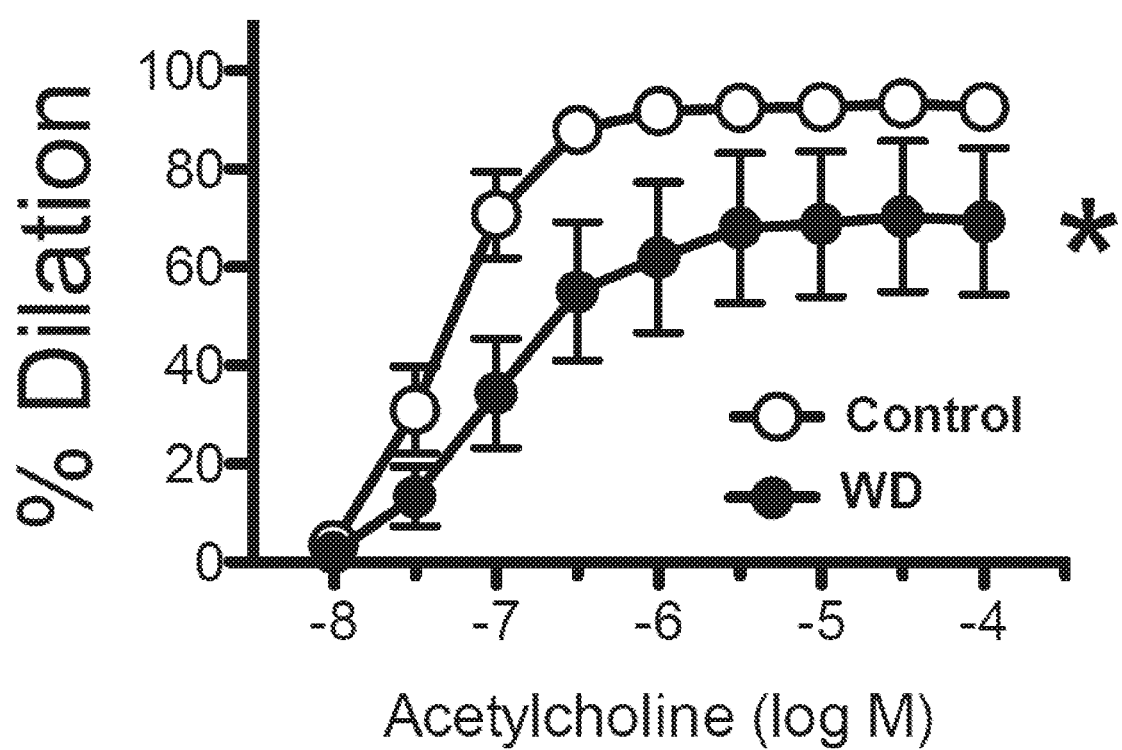
FIG. 1 is a graph depicting impaired endothelial function in femoral resistance arteries from Western diet (WD) fed mice. Data are expressed as means±SEM. *P<0.05 vs. Control.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Suitable dosages of the neuraminidase inhibitor for use in the methods of the present disclosure will depend upon a number of factors including, for example, age and weight of an individual, severity of glycocalyx damage, specific neuraminidase inhibitor to be used, nature of a composition, route of administration and combinations thereof. Ultimately, a suitable dosage can be readily determined by one skilled in the art such as, for example, a physician, a veterinarian, a scientist, and other medical and research professionals. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result.

Pharmaceutically acceptable carriers can be, for example, excipients, vehicles, diluents, and combinations thereof. For example, where the compositions are to be administered orally, they may be formulated as tablets, capsules, granules, powders, or syrups; or for parenteral administration, they may be formulated as injections (intramuscular, subcutaneous, intramedullary, intrathecal, intraventricular, intravenous, intravitreal), drop infusion preparations, or suppositories. These compositions can be prepared by conventional means, and, if desired, the active compound (i.e., neuraminidase inhibitor) may be mixed with any conventional additive, such as an excipient, a binder, a disintegrating agent, a lubricant, a corrigent, a solubilizing agent, a suspension aid, an emulsifying agent, a coating agent, or combinations thereof.

It should be understood that the pharmaceutical compositions of the present disclosure can further include additional known therapeutic agents, drugs, modifications of the synthetic compounds into prodrugs, and the like for alleviating, mediating, preventing, and treating the diseases, disorders, and conditions described herein.

The pharmaceutical compositions including a neuraminidase inhibitor and/or pharmaceutical carriers used in the methods of the present disclosure can be administered to a subset of individuals in need. As used herein, an "individual in need" refers to an individual having or suspected of having diabetes, and in particular, having or suspected of having type 1 diabetes and having or suspected of having type 2 diabetes, an individual having or suspected of having coronary artery disease, an individual having or suspected of having peripheral vascular disease, an individual having or suspected of having cerebrovascular disease, an individual having or suspected of having atherosclerosis, an individual having or suspected of having hypertension, an individual having or suspected of having ischemic diseases (stroke), an individual having or suspected of having pulmonary diseases (asthma, acute lung injury and ventilator-induced lung injury), an individual having or suspected of having ocular diseases (diabetic retinopathy), and combinations thereof. Additionally, an "individual in need" is also used herein to refer to an individual at risk for or diagnosed by a medical professional as having or suspected of having diabetes, and in particular, type 1 diabetes and type 2 diabetes, an individual having or suspected of having coronary artery disease, an individual having or suspected of having peripheral vascular disease, an individual having or suspected of having cerebrovascular disease, an individual having or suspected of having atherosclerosis, an individual having or suspected of having hypertension, an individual having or suspected of having ischemic diseases (stroke), an individual having or suspected of having pulmonary diseases (asthma, acute lung injury and ventilator-induced lung injury), an individual having or suspected of having ocular diseases (diabetic retinopathy), and combinations thereof. As such, in some embodiments, the methods disclosed herein are directed to a subset of the general population such that, in these embodiments, not all of the general population may benefit from the methods. Based on the foregoing, because some of the method embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein. In particular, the individual in need is a human. The individual in need can also be, for example, a pet (companion animal) such as, for example, a dog, a cat, etc., a research animal such as, for example, a non-human primate, a mouse, a rat, a rabbit, a cow, a pig, and other types of research animals known to those skilled in the art.

Suitable neuraminidase inhibitors can be Neu5Ac2en ((2R,3R,4S)-3-acetamido-4-hydroxy-2-[(1R,2R)-1,2,3-trihydroxypropyl]-3,4-dihydro-2H-pyran-6-carboxylic acid), as well as all Neu5Ac2en derivatives including (2R,3R,4S)-3-acetamido-4-amino-2-[(1R,2R)-1,2,3-trihydroxypropyl]-3,4-dihydro-2H-pyran-6-carboxylic acid, zanamivir (5-acetamido-4-guanidino-6-(1,2,3-trihydroxypropyl)-5,6-dihydro-4H-pyran-2-carboxylic acid), laninamivir ((4S,5R,6R)-5-acetamido-4-carbamimidamido-6-[(1R,2R)-3-hydroxy-2-methoxypropyl]-5,6-dihydro-4H-pyran-2-carboxylic acid), and peramivir ((1S,2S,3R,4R)-3-[(1S)-1-(Acetylamino)-2-ethylbutyl]-4-(carbamimidoylamino)-2-hydroxycyclopentanecarboxylic acid). Additional inhibitors can be oseltamivir (ethyl (3R,4R,5S)-5-amino-4-acetamido-3-(pentan-3-yloxy)-cyclohex-1-ene-1-carboxylate), siastatin B ((3S,4S,5R,6R)-6-acetamido-4,5-dihydroxypiperidine-3-carboxylic acid) and all analogs/derivatives of siastatin B, as well as all other sialidases that hydrolyze alpha(2-3)-, alpha(2-6)-, and alpha(2-8)-glycosidic linkages of terminal sialic residues.

Suitable routes of administration include, for example, intravenous, inhalation, intraperitoneal (i.p.), parenteral, subcutaneous, intra-articular, and intramuscular.

In one aspect, the present disclosure is directed to a method for ameliorating glycocalyx damage in an individual in need thereof. The method includes: administering to the individual in need thereof a composition comprising a neuraminidase inhibitor.

Without being bound by theory it is believed that ameliorating glycocalyx damage by inhibiting or reducing neuraminidase activity can result in improved arterial flow mediated dilation, improved endothelial function (e.g., nitric oxide production), improved vascular permeability, reduced platelet aggregation, reduced leukocyte adhesion, and combinations thereof.

In one aspect, the present disclosure is directed to a method for treating endothelial dysfunction in an individual in need thereof. The method includes: administering to the individual in need thereof a composition comprising a neuraminidase inhibitor.

Suitable neuraminidase inhibitors can be Neu5Ac2en ((2R,3R,4S)-3-acetamido-4-hydroxy-2-[(1R,2R)-1,2,3-trihydroxypropyl]-3,4-dihydro-2H-pyran-6-carboxylic acid), as well as all Neu5Ac2en derivatives including (2R,3R,4S)-3-acetamido-4-amino-2-[(1R,2R)-1,2,3-trihydroxypropyl]-3,4-dihydro-2H-pyran-6-carboxylic acid, zanamivir (5-acetamido-4-guanidino-6-(1,2,3-trihydroxypropyl)-5,6-dihydro-4H-pyran-2-carboxylic acid), laninamivir ((4S,5R,6R)-5-acetamido-4-carbamimidamido-6-[(1R,2R)-3-hydroxy-2-methoxypropyl]-5,6-dihydro-4H-pyran-2-carboxylic acid), and peramivir ((1S,2S,3R,4R)-3-[(1S)-1-(Acetylamino)-2-ethylbutyl]-4-(carbamimidoylamino)-2-hydroxycyclopentanecarboxylic acid). Additional inhibitors can be oseltamivir (ethyl (3R,4R,5S)-5-amino-4-acetamido-3-(pentan-3-yloxy)-cyclohex-1-ene-1-carboxylate), siastatin B ((3S,4S,5R,6R)-6-acetamido-4,5-dihydroxypiperidine-3-carboxylic acid) and all analogs/derivatives of siastatin B, as well as all other sialidases that hydrolyze alpha(2-3)-, alpha(2-6)-, and alpha(2-8)-glycosidic linkages of terminal sialic residues.

Suitable routes of administration include, for example, intravenous, inhalation, intraperitoneal (i.p.), parenteral, subcutaneous, intra-articular, and intramuscular.

In one aspect, the present disclosure is directed to a method for improving flow mediated dilation in an individual in need thereof. The method includes: administering to the individual in need thereof a composition comprising a neuraminidase inhibitor. As used herein, "improved" flow mediated dilation refers to increasing blood vessel diameter in response to blood flow. Flow of blood exerts a shear-stress on arterial walls initiating a biochemical response causing the vessel to dilate. Dilation is compromised in a number of cardiovascular pathologies, including those associated with diabetes. Flow mediated dilation can be measured using methods known to those skilled in the art such as, for example, ultrasound and as described in the Examples. Blood vessel diameters are assessed under baseline conditions followed by inflation of a sphygmomanometer cuff to restrict blood flow and then compared to diameters following deflation of the cuff resulting in increased blood flow and shear stress. An increase in blood vessel diameter in response to blood flow represents an improved flow mediated dilation.

Suitable neuraminidase inhibitors can be Neu5Ac2en ((2R,3R,4S)-3-acetamido-4-hydroxy-2-[(1R,2R)-1,2,3-trihydroxypropyl]-3,4-dihydro-2H-pyran-6-carboxylic acid), as well as all Neu5Ac2en derivatives including (2R,3R,4S)-3-acetamido-4-amino-2-[(1R,2R)-1,2,3-trihydroxypropyl]-3,4-dihydro-2H-pyran-6-carboxylic acid, zanamivir (5-acetamido-4-guanidino-6-(1,2,3-trihydroxypropyl)-5,6-dihydro-4H-pyran-2-carboxylic acid), laninamivir ((4S,5R,6R)-5-acetamido-4-carbamimidamido-6-[(1R,2R)-3-hydroxy-2-methoxypropyl]-5,6-dihydro-4H-pyran-2-carboxylic acid), and peramivir ((1S,2S,3R,4R)-3-[(1S)-1-(Acetylamino)-2-ethylbutyl]-4-(carbamimidoylamino)-2-hydroxycyclopentanecarboxylic acid). Additional inhibitors can be oseltamivir (ethyl (3R,4R,5S)-5-amino-4-acetamido-3-(pentan-3-yloxy)-cyclohex-1-ene-1-carboxylate), siastatin B ((3S,4S,5R,6R)-6-acetamido-4,5-dihydroxypiperidine-3-carboxylic acid) and all analogs/derivatives of siastatin B, as well as all other sialidases that hydrolyze alpha(2-3)-, alpha(2-6)-, and alpha(2-8)-glycosidic linkages of terminal sialic residues.

Suitable routes of administration include, for example, intravenous, inhalation, orally, intraperitoneal (i.p.), parenteral, subcutaneous, intra-articular, and intramuscular.

Suitable individuals in need thereof include those having or suspected of having diabetes. Particularly suitable individuals in need thereof include those having or suspected of having type 2 diabetes.

Various functions and advantages of these and other embodiments of the present disclosure will be more fully understood from the examples shown below. The examples are intended to illustrate the benefits of the present disclosure, but do not exemplify the full scope of the disclosure.

EXAMPLES

Example 1

In this Example, endothelial function in resistance vessels was determined in Western diet-fed mice.

Femoral resistance arteries from Control and Western diet-fed (WD) mice were isolated, cannulated, and subjected to physiological pressure (70 mmHg) and temperature (37° C.). For WD-fed mice, groups of 4-week old C57/BL6 male mice were fed a diet consisting of high fat (46%) and high carbohydrate as sucrose (17.5%) and high-fructose corn syrup (17.5%) for 16 weeks. A parallel group of age-matched male controls were fed regular mouse chow for the same period of time. Vessels were pre-constricted and exposed to increasing concentrations of acetylcholine. As depicted in FIG. 1, femoral arteries from WD-fed mice had a significantly reduced vasodilatory response to acetylcholine versus control mice.

Figure 2A:
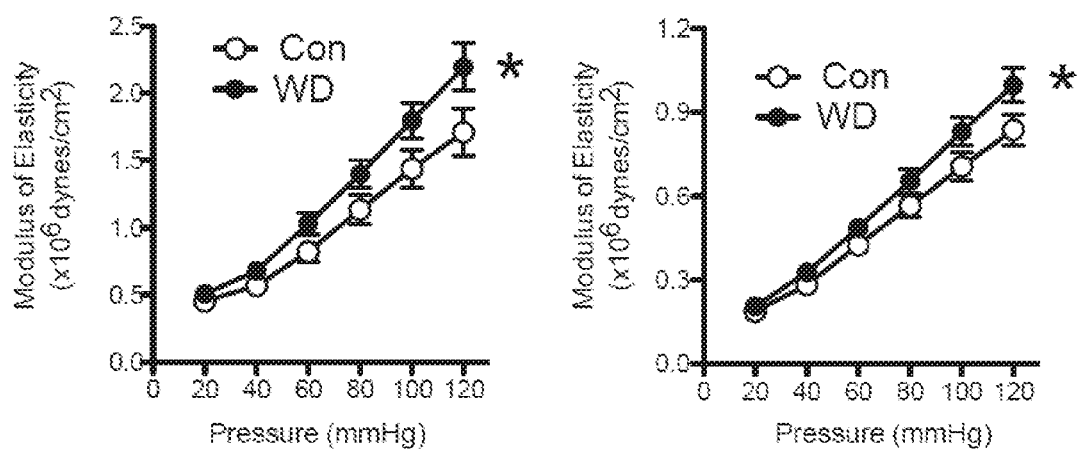
FIGS. 2A and 2B are graphs depicting moduli of elasticity (stiffness) of mesenteric and femoral arteries from control and WD-fed mice (FIG. 2A) and strain vs. stress curves of mesenteric and femoral arties from control and WD-fed mice (FIG. 2B). Data are expressed as means±SEM, *P<0.05 vs. control.
Figure 2B:
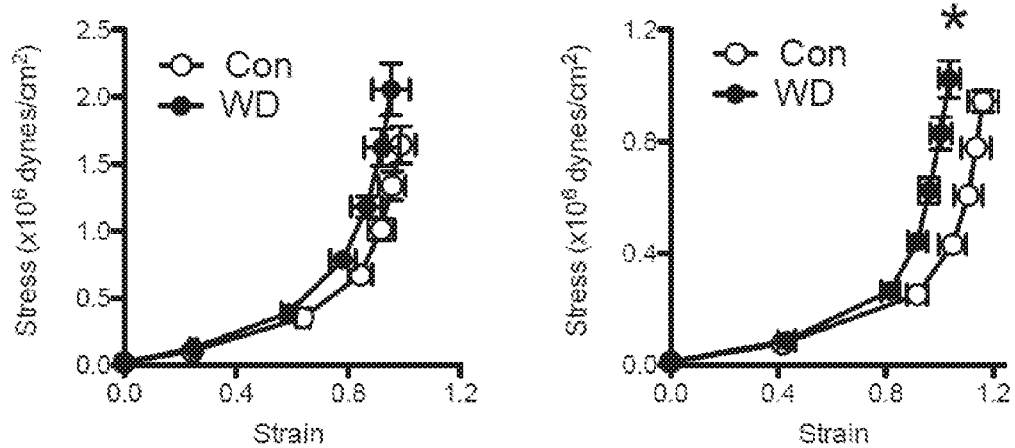

Mesenteric and femoral arteries from Control and WD-fed mice were isolated, cannulated and subjected to incremental increases in luminal pressure in physiological saline at 37° C. Moduli of elasticity (stiffness) and strain versus stress curves of mesenteric and femoral arteries were determined. All measurements were made under passive conditions ($Ca^{2+}$-free PSS+$10^{-4}$ M adenosine+2 mM EGTA). As depicted in FIGS. 2A and 2B, Western diet increased vascular stiffness.

Example 2

In this Example, plasma neuraminidase activity was determined in WD-fed mice.

Figure 3:
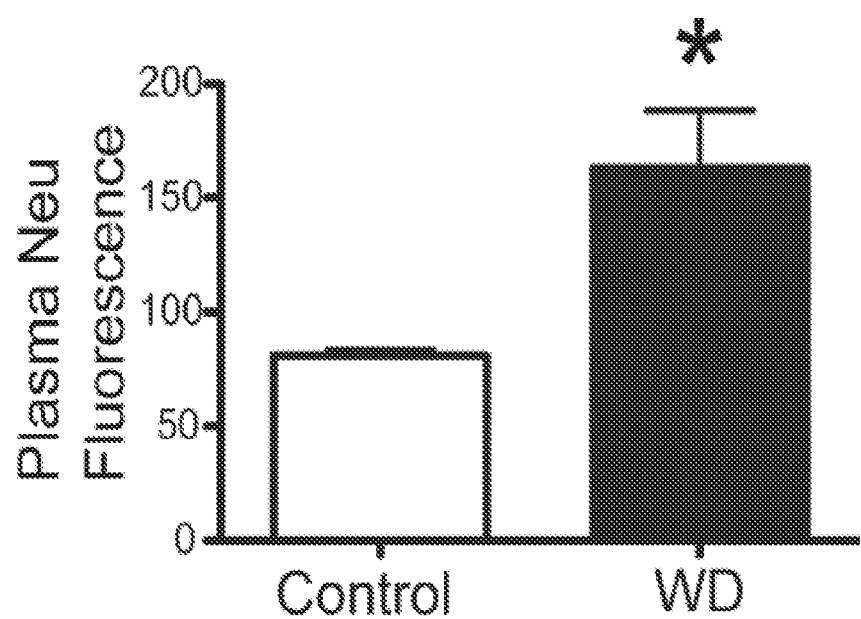
FIG. 3 is a graph depicting plasma neuraminidase (desialylation) activity in mice fed a control diet and WD. Data are expressed as means±SEM. *P<0.05 vs. Control.

Male mice were fed a Western diet or control diet. Plasma was isolated and assessed for neuraminidase (desialylation) activity using a commercial kit (Amplex Red Neuraminidase Assay Kit, A22178, Molecular Probes). Level (arbitrary units) of fluorescence induced by neuraminidase (Neu) activity in plasma obtained from control (n=4) and WD-fed mice (n=4). As depicted in FIG. 3, a Western diet increased plasma neuraminidase activity.

Example 3

In this Example, glycocalyx protection as a result of neuraminidase inhibition was tested.

Figure 4A:
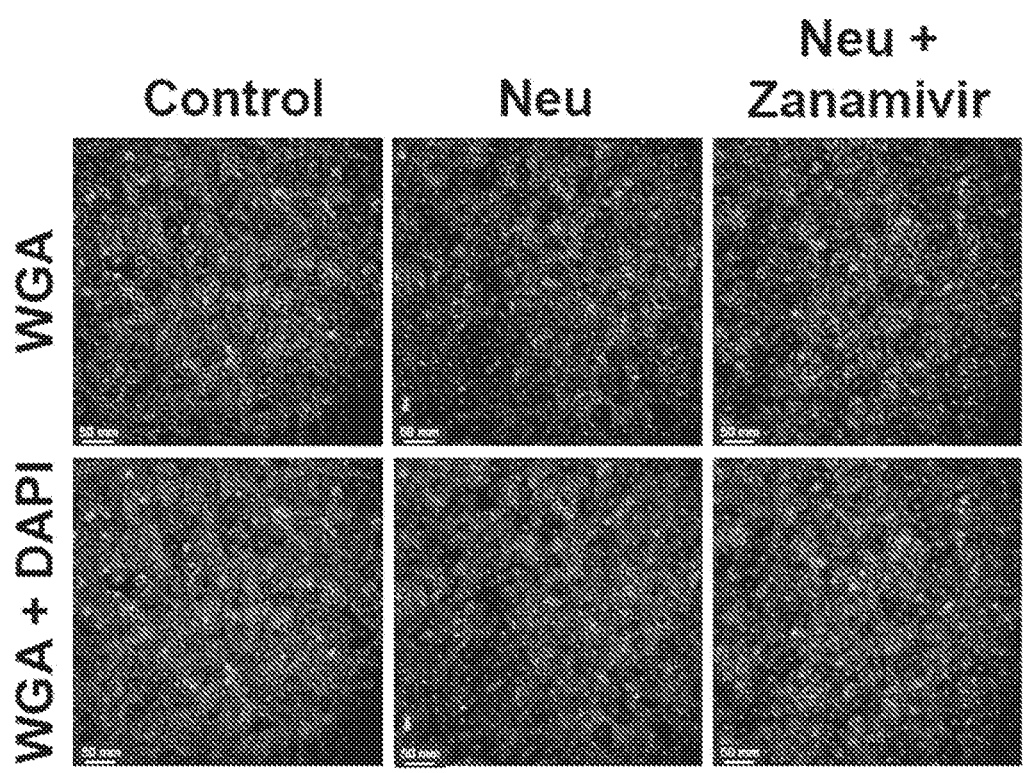
FIGS. 4A-4F are representative images and graphs depicting neuraminidase degradation of the glycocalyx in cell culture Immunofluorescence analysis of the glycocalyx of human endothelial cells labelled with Wheat Germ Agglutinin-488 (upper panels represent green channel) and nuclei labelled with DAPI (lower panels represent overlay of green and blue channels) treated for 1 hour with either vehicle/control, neuraminidase, or neuraminidase+Zanamivir (FIG. 4A). Neuraminidase treatment facilitated a significant reduction in WGA staining intensity, which was attenuated in the presence of Zanamivir (FIG. 4B). Immunofluorescence analysis of Syndecan-1 staining in human endothelial cells Syndecan-1/FITC (upper panels represent green channel) and nuclei labelled with DAPI (lower panels represent overlay of green and blue channels) following 1 hour neuraminidase or control/vehicle treatment (FIG. 4C). Neuraminidase treatment facilitated a significant reduction in Syndecan-1 staining intensity (FIG. 4D). Western blot analysis using Syndecan-1 antibody of total lysates from human endothelial cells pre-treated for 1 hour with vehicle/control or neuraminidase and subsequently exposed to 15 dynes/cm² shear stress for 1 hour (FIG. 4E). Syndecan-1 protein/μg total cell lysate is significantly reduced in the neuraminidase treated cohort vs the vehicle/control (FIG. 4F). All data are expressed as means±SEM, *P<0.05 vs. control.
Figure 4B:
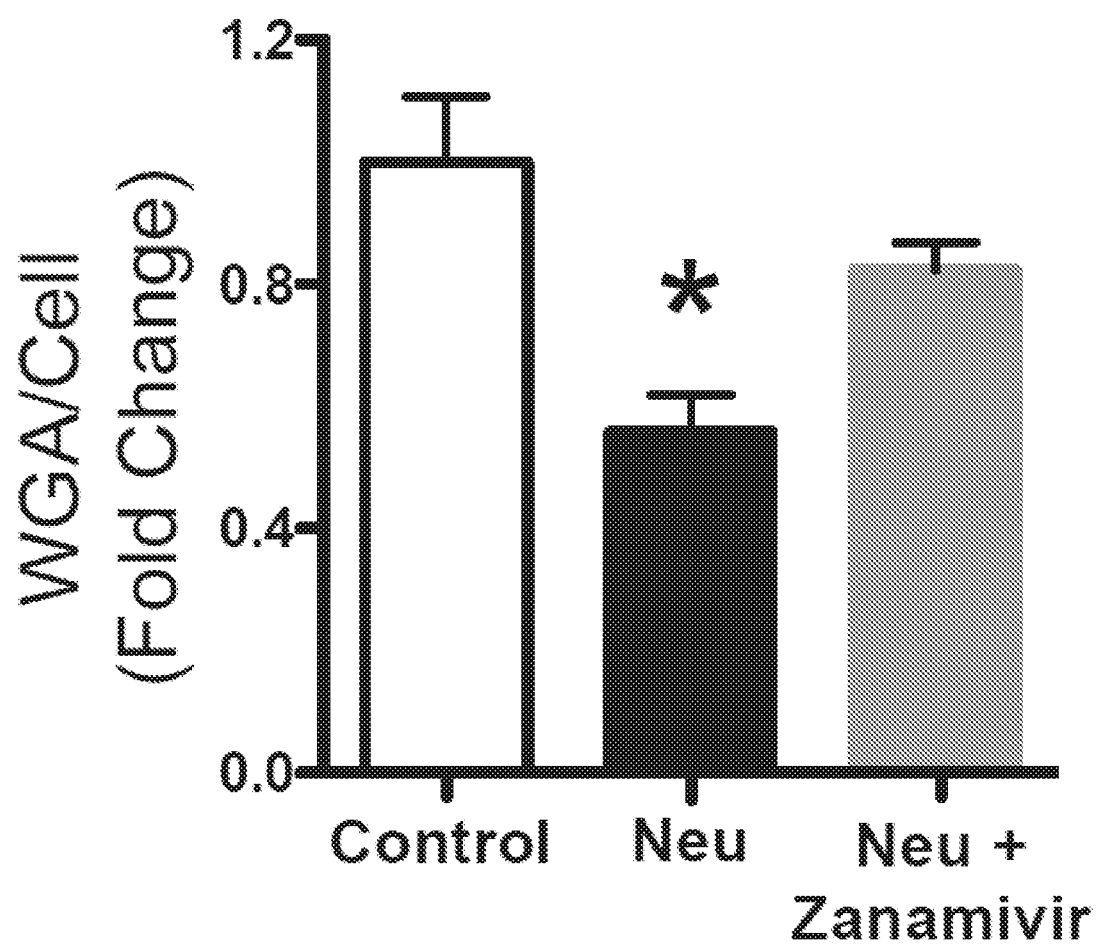

Human endothelial cells were cultured and treated with vehicle (control; n=8), neuraminidase (n=8), or neuraminidase plus Zanamivir (n=8) for 1 hour, then stained with WGA (Green) to measure glycocalyx intensity and DAPI (blue) to stain cell nuclei. As depicted in FIGS. 4A and 4B, neuraminidase treatment facilitated a significant reduction in wheat germ agglutinin (WGA), which was attenuated in the presence of Zanamivir.

Figure 4C:
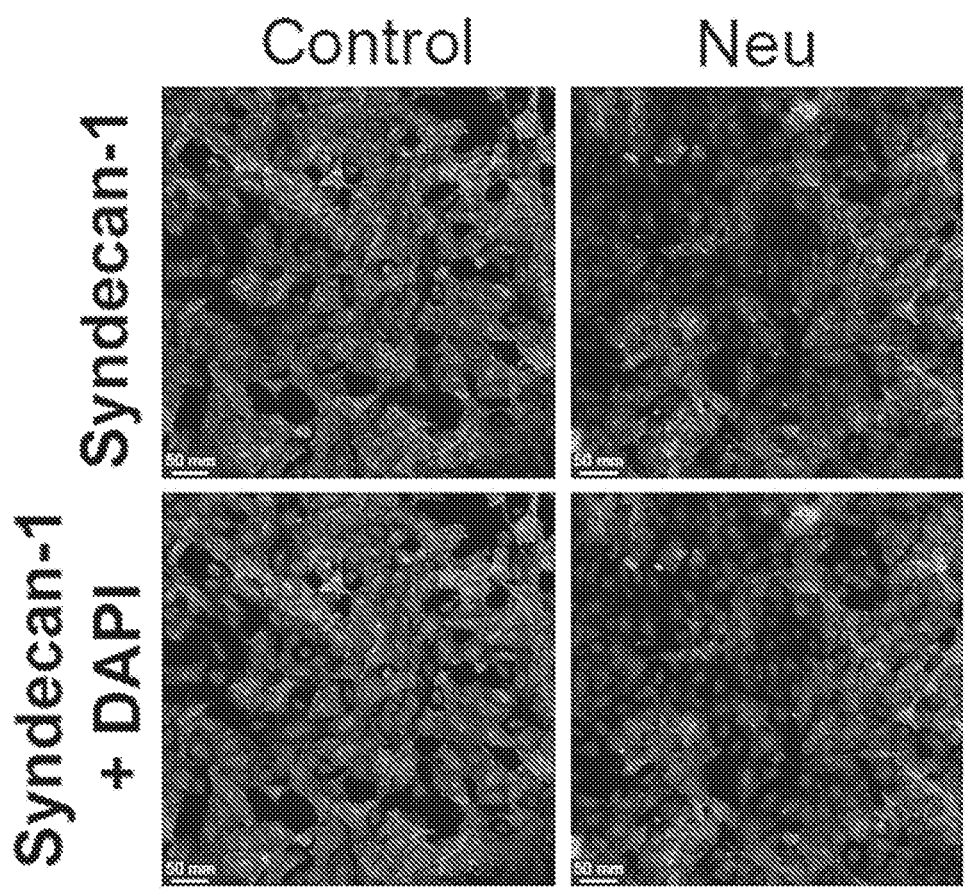
Figure 4D:
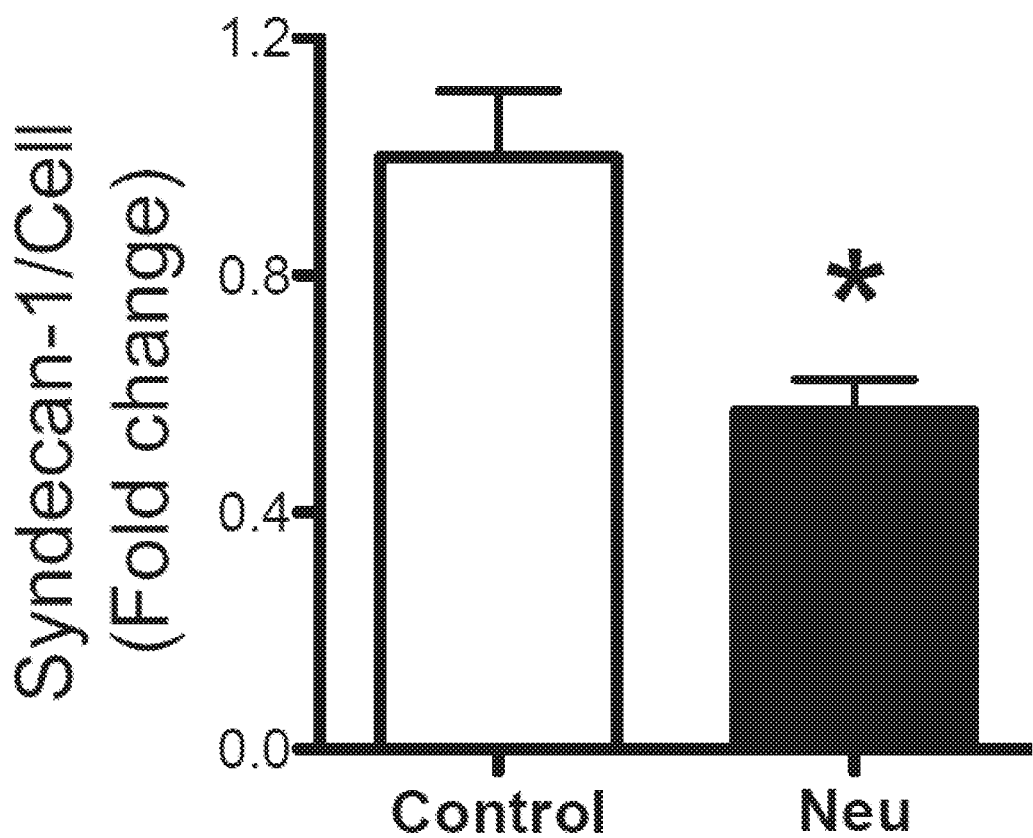

As depicted in FIGS. 4C and 4D, a second marker of glycocalyx integrity, Syndecan-1, was measured by treating human endothelial cells in culture for 1-hour with neuraminidase (N=4) vs. the vehicle treated control (N=4), followed by immunofluorescence with Syndecan-1 antibody (green) and DAPI (blue).

Figure 4E:
Figure 4F:
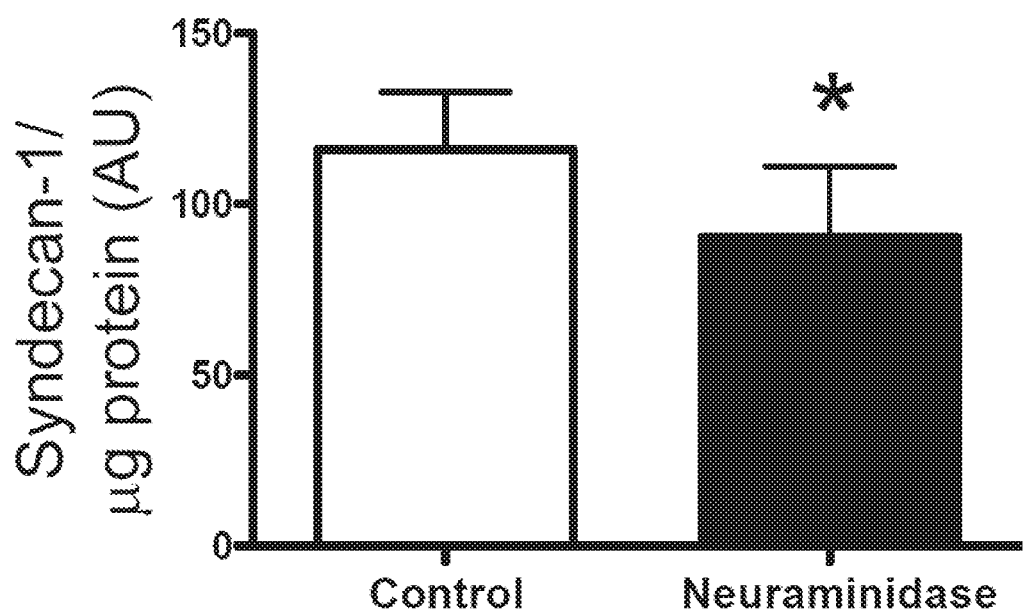

FIGS. 4E and 4F show, via Western Blot analysis using Syndecan-1 antibody of total lysates from human endothelial cells pre-treated for 1 hr. with vehicle/control (n=8) or neuraminidase (n=8) and subsequently exposed to 15 dynes/$cm^2$ shear stress for 1 hr., that Syndecan-1 protein/µg total cell lysate is significantly reduced in the neuraminidase treated cohort vs the vehicle/control. Data represent mean+/−SEM. *$P<0.05$, determined by two-tailed Student t test.

Example 4

In this Example, mesenteric arteries were treated intraluminally with control solution or with neuraminidase and stained to image the glycocalyx. Note that neuraminidase treatment damaged the glycocalyx.

Figure 5:
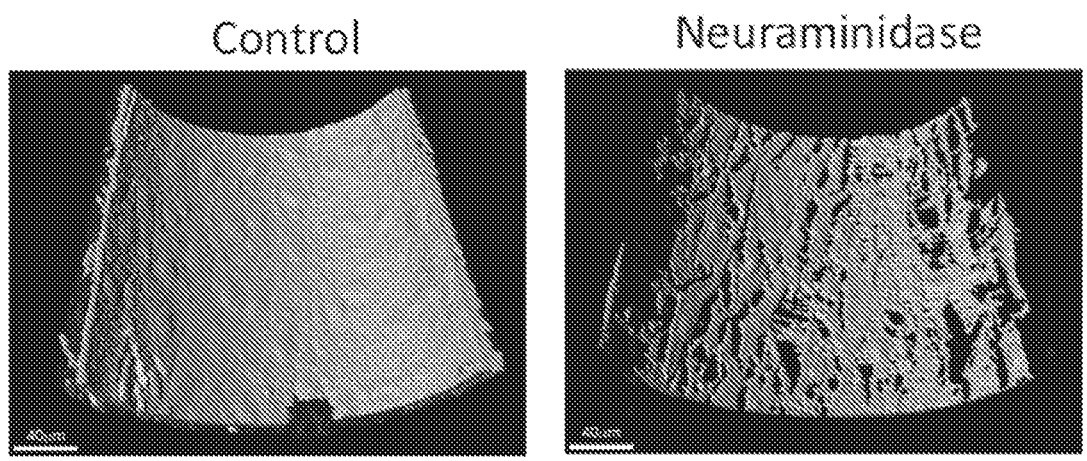
FIG. 5 shows fluorescence microscope images depicting intraluminal treatment of mesenteric arteries control solution (left panel) or neuraminidase (right panel), and stained with Wheat Germ Agglutinin-488 (green channel) to image the glycocalyx and DAPI (blue channel) to image nuclei in control (left panel) and neuraminidase-treated arteries (right panel).

Mesenteric arteries were treated intraluminally for 1 hour with either vehicle (control) or 50 mU/ml neuraminidase. As depicted in FIG. 5, tissue was stained with Wheat Germ Agglutinin-488 to image the glycocalyx and DAPI to image nuclei. An algorithm was applied to the green channel (glycocalyx image) to volumetrically represent the glycocalyx. Control volume was 3.54 µm³. Neuraminidase volume was 1.87 µm³, which represented a 47% reduction in glycocalyx volume in arteries treated with neuraminidase.

Example 5

In this Example, flow mediated dilation was determined in control or neuraminidase treated mesenteric arteries.

Figure 6A:
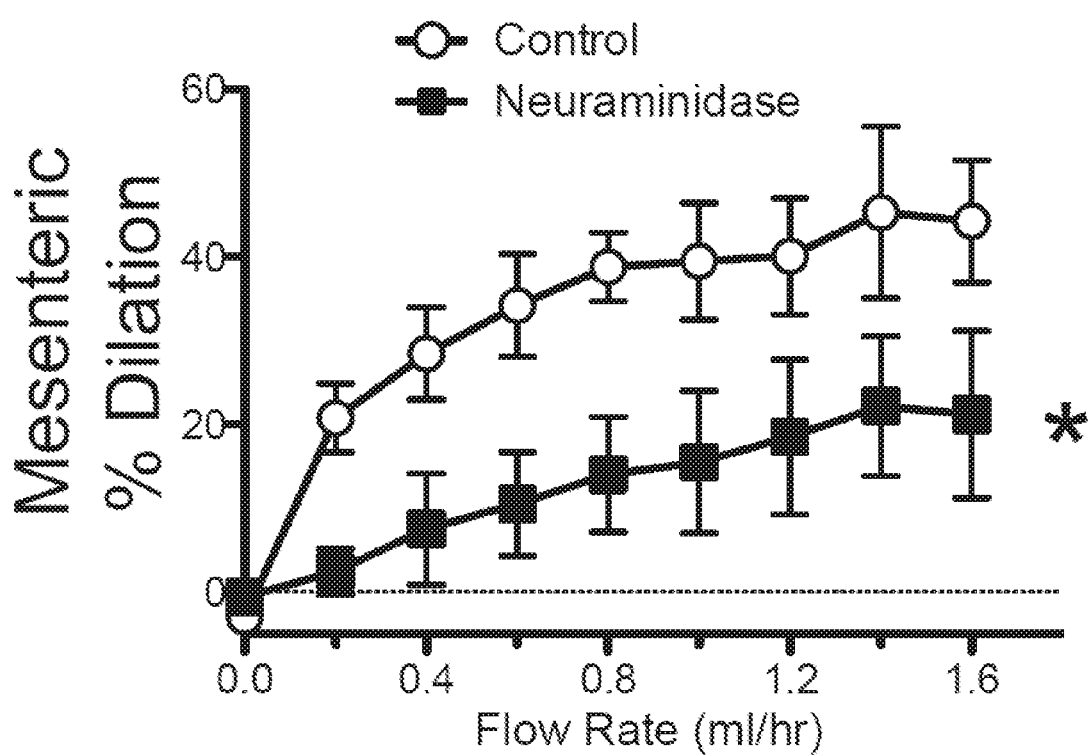
FIGS. 6A and 6B are graphs depicting intraluminal treatment of mesenteric arteries from control mice with control solution or neuraminidase (Neu), pre-constricted with phenylephrine and exposed to incremental increases in continuous flow rate to subject the vessel wall to increasing shear stress. *P<0.05, for all flow rates vs. Control. Data are means±SEM.
Figure 6B:
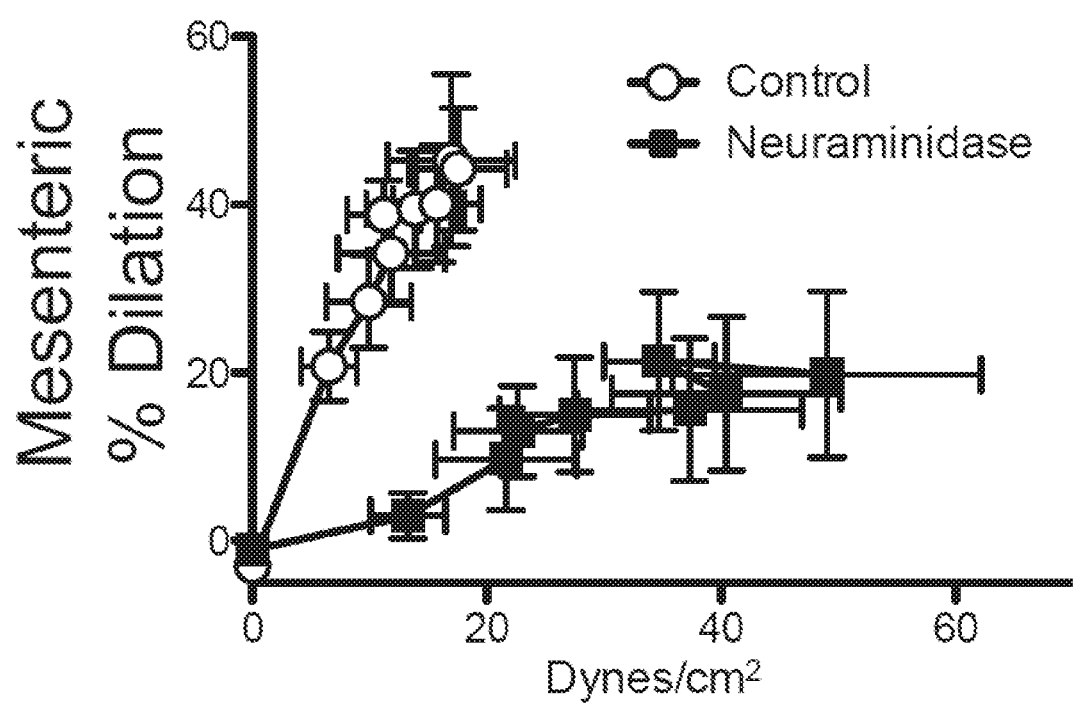

Pressurized, cannulated, mesenteric arteries from control mice were pretreated with vehicle/control (n=6) or 50 mU/ml neuraminidase (n=5) for 1 hr., pre-constricted with $10^{-6}$ M phenylephrine and exposed to increasing flow rates to subject the vessel wall to increasing shear stresses. FIG. 6A shows neuraminidase had a significant negative effect on flow mediated dilation responses compared to controls. FIG. 6B represents the same experiment, but with data graphed at Dynes/cm2 vs. Mesenteric % Dilation. Data represent mean+/−SEM, *P<0.05, determined by two-tailed Student t test.

Percent dilation is expressed as:

$$\frac{\text{(Flow Rate Diameter} - \text{Constricted Diameter)}}{\text{(Max. Passive Diameter} - \text{Constricted Diameter)}} \times 100$$

Figure 6C:
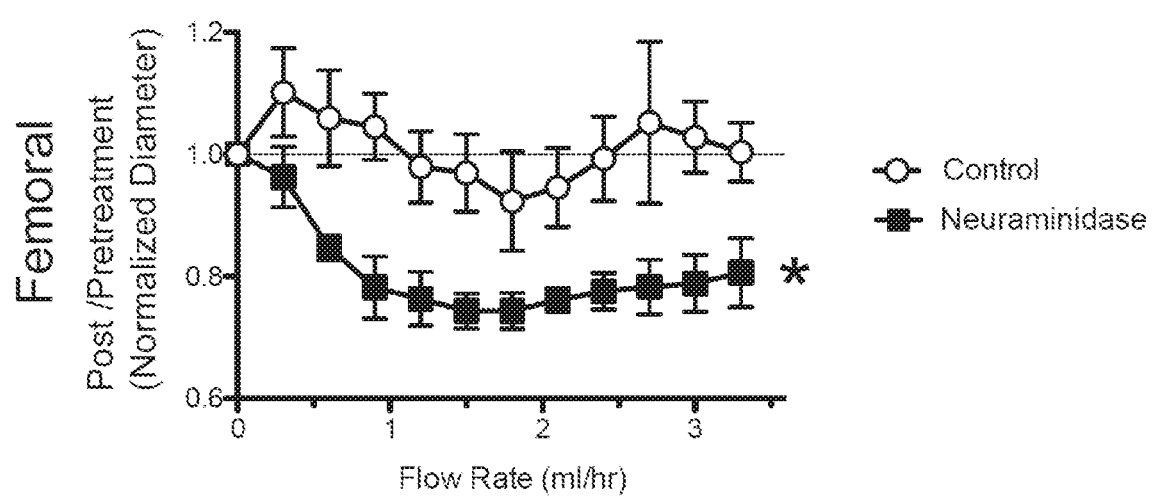
(FIG. 6 C) Femoral arteries from control mice were pre-constricted with phenylephrine and assessed for flow mediated dilation. Vessels were then treated with either vehicle/control or neuraminidase for 1 hour and reassessed for flow mediated dilation. Data expressed as the normalized post-treatment pre-constricted diameter/normalized pretreatment pre-constricted diameter. Data represent mean+/−SEM, *P<0.05.

FIG. 6C shows further evidence that neuraminidase treatment blunts flow mediated dilation (FMD) in isolated mouse arteries. Femoral arteries from control mice were pre-constricted with phenylephrine and assessed for FMD. Vessels were then treated with either vehicle control (n=5) or neuraminidase (n=4) for 1 hour and reassessed for FMD. Data are expressed as the normalized post-treatment pre-constricted diameter/normalized pretreatment pre-constricted diameter. Data represent mean+/−SEM, *P<0.05, determined by two-tailed paired Student t test.

Example 6

In this Example, flow mediated dilation as well as plasma neuraminidase activity and sialic acid levels were measured in patients with or without type 2 diabetes.

Figure 7A:
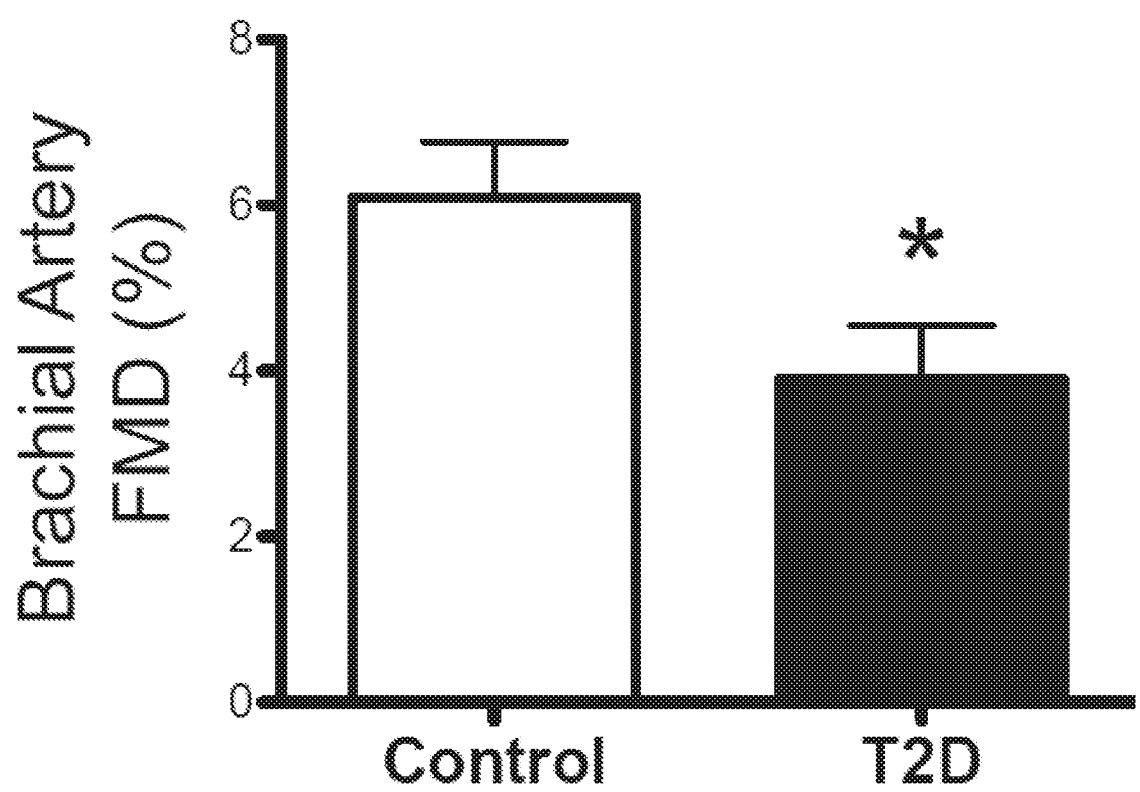
FIG. 7A is a graph depicting flow mediated dilation in healthy (non-diabetic) patients and patients with type 2 diabetes (T2D).

Ultrasound was used to measure flow mediated dilation in healthy (non-diabetic) patients (n=8) and patients with type 2 diabetes (T2D) (n=8). Brachial artery diameters were assessed under baseline conditions followed by inflation of a sphygmomanometer cuff to restrict blood flow (ischemia) and compared to diameters following deflation of the cuff resulting in increased blood flow (hyperemia) and shear stress. As depicted in FIG. 7A, T2D patients exhibited impaired peripheral artery flow-mediated dilation. Data represent mean+/−SEM, *P<0.05, determined by two-tailed Student t test.

Flow mediated dilation was expressed as:

$$\frac{\text{hyperemic diameter} - \text{baseline diameter}}{\text{baseline diameter}} \times 100$$

Figure 7B:
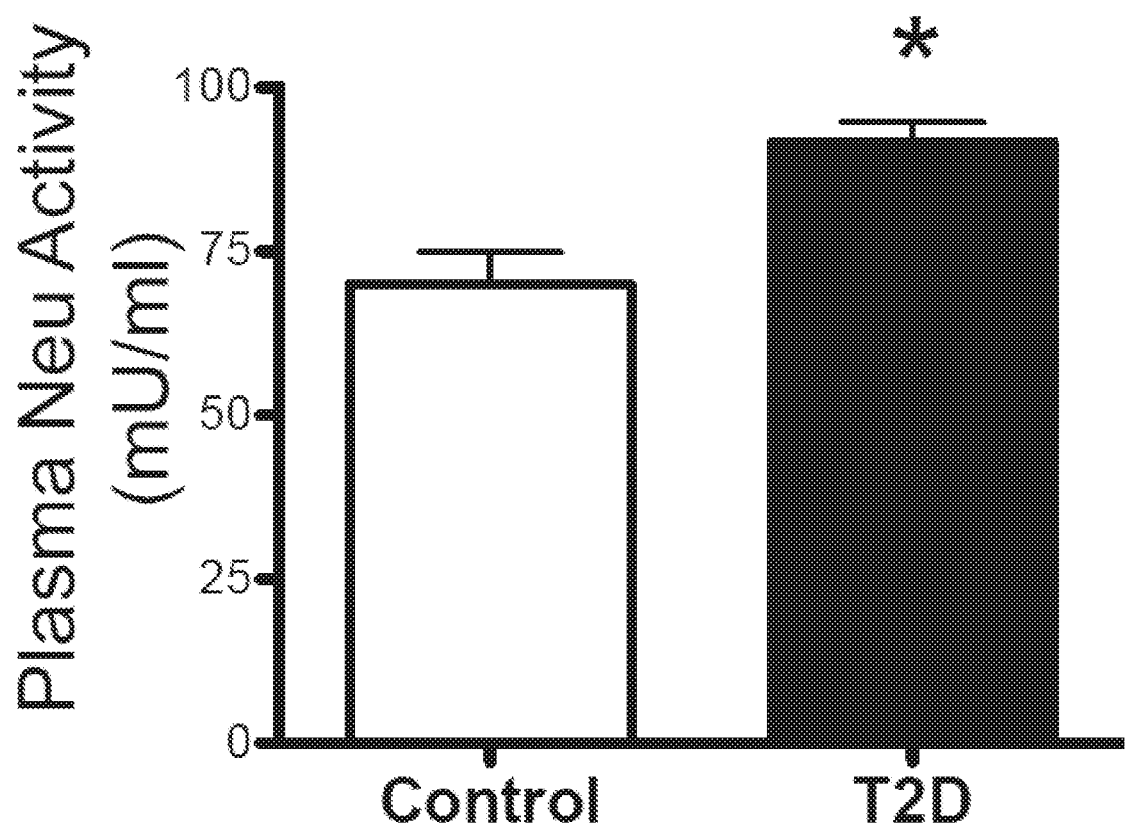
FIG. 7B is a graph depicting neuraminidase activity in healthy (non-diabetic) patients and patients with type 2 diabetes (T2D).
Figure 7C:
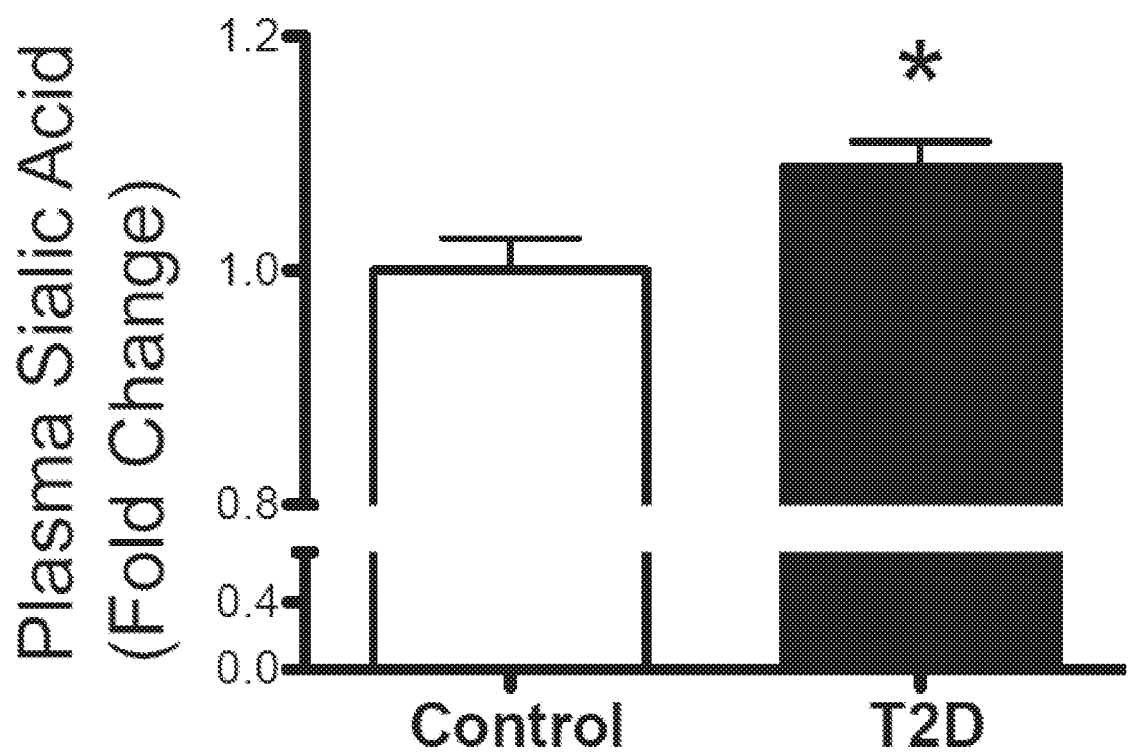
FIG. 7C is a graph depicting sialic acid levels in healthy (non-diabetic) patients and patients with type 2 diabetes (T2D).

Plasma from the same control and T2D cohorts was analyzed for neuraminidase activity as well as sialic acid levels. Neuraminidase activity was assessed by measuring the release of 4-Methylumbelliferone from the fluorogenic substrate 4MU-NANA incubated with plasma samples. Sialic acid levels were measured using a commercial ELISA assay kit (ab83375, Abcam). Neuraminidase activity was significantly elevated (FIG. 7B) in the T2D cohort (n=8) versus the control (n=8). Sialic acid levels were also elevated (FIG. 7C) in the T2D cohort (n=7) compared to the controls (n=8). Data represent mean+/−SEM, *P<0.05, determined by two-tailed Student t test.

Example 7

In this Example, the effect of the neuraminidase inhibitor, Zanamivir, was assessed in a mouse model of type 2 diabetes on plasma neuraminidase activity, as well as flow mediated dilation and endothelial dependent vasodilation in isolated arteries.

Male, 12-week old db/db mice were administered twice a day via inhalation either 5 mg of the neuraminidase inhibitor, Zanamivir or lactose as placebo control, for 5 days.

Figure 8A:
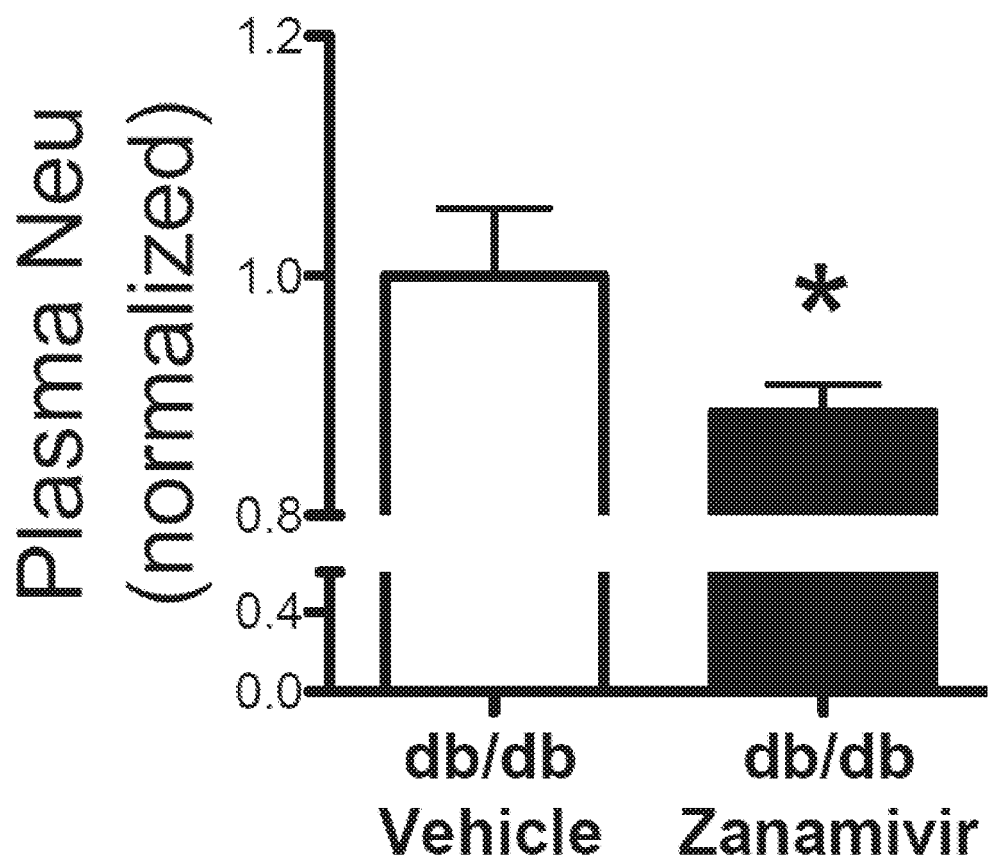
FIG. 8A is a graph depicting plasma neuraminidase activity in db/db mice (a mouse model of type 2 diabetes) treated with a neuraminidase inhibitor (Zanamivir) or placebo control. Data expressed as means±SEM. *P<0.05 vs. Control.

Plasma was isolated and assessed for neuraminidase (desialylation) activity using a commercial kit (Amplex Red Neuraminidase Assay Kit, A22178, Molecular Probes). Level (arbitrary units) of fluorescence induced by neuraminidase (Neu) activity in plasma obtained from Control (n=8) and Zanamivir treated db/db mice (n=8). As depicted in FIG. 8A, db/db mice treated with Zanamivir had significantly reduced plasma neuraminidase activity compared to placebo control treated db/db mice. Data represent mean+/−SEM, *P<0.05, determined by one-tailed Student t test.

Figure 8B:
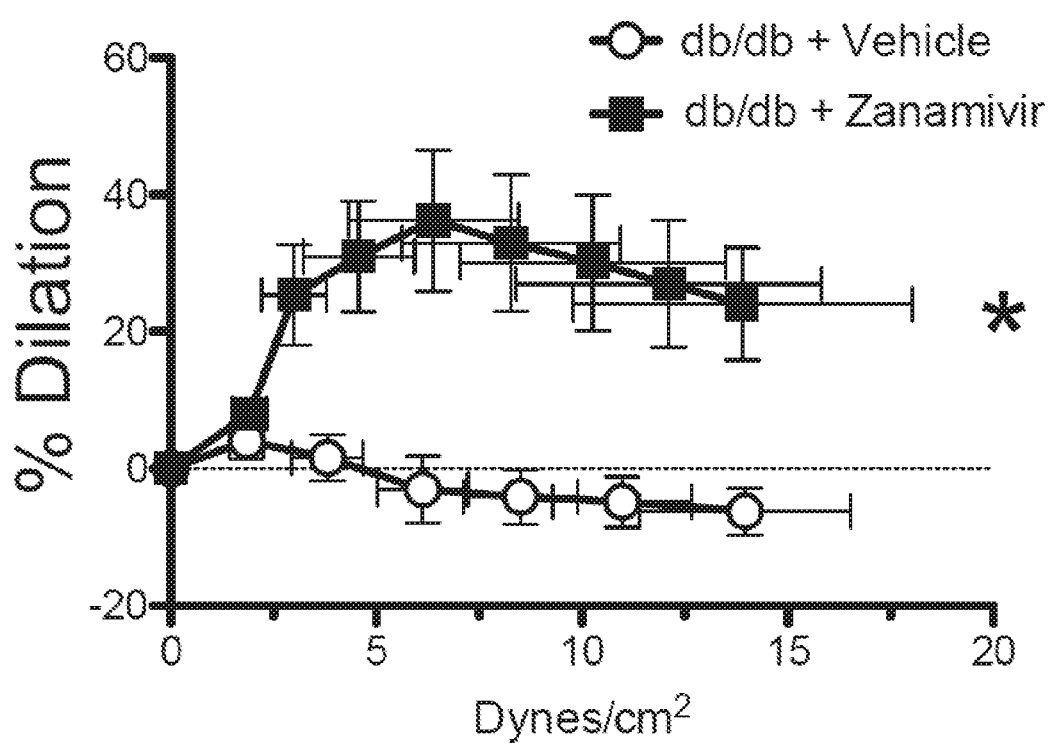
FIG. 8B is a graph depicting flow mediated dilation in isolated femoral arteries from db/db mice (a mouse model of diabetes) treated with a neuraminidase inhibitor (Zanamivir) or control. Data expressed as means±SEM. *P<0.05 vs. Control.

Femoral arteries from placebo control and Zanamivir treated mice were isolated, cannulated and pressurized in physiological saline at 37° C. Vessels were pre-constricted with phenylephrine and exposed to increasing shear stress (dynes/cm²) to assess flow mediated dilation. As depicted in FIG. 8B, femoral arteries from Zanamivir treated db/db mice (n=5) displayed significantly improved flow mediated dilation compared to arteries from placebo control treated db/db mice (n=6). Data represent mean+/−SEM, *P<0.05, determined by two-tailed Student t test.

Figure 8C:
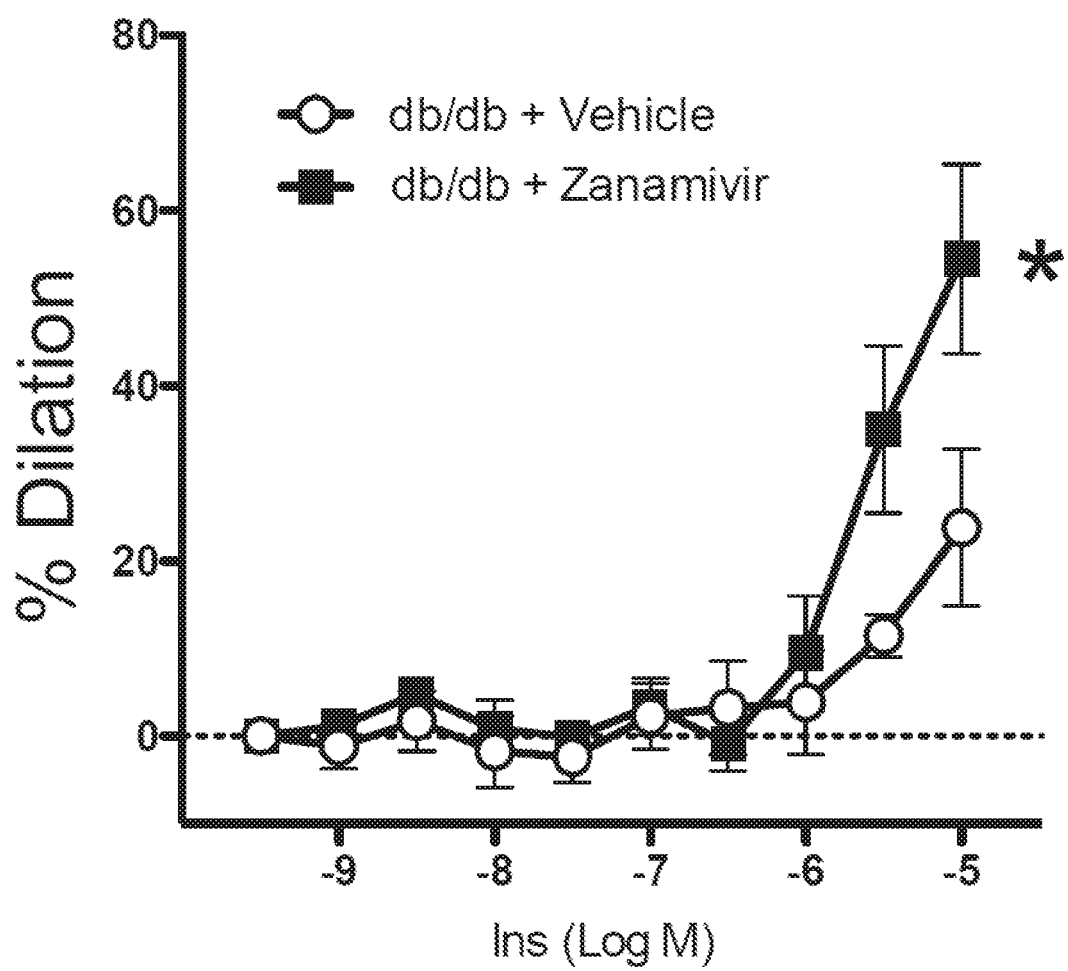
FIG. 8C is a graph depicting improved endothelial dependent vasodilation to insulin in isolated femoral arteries from db/db mice (a mouse model of type 2 diabetes) treated with a neuraminidase inhibitor (Zanamivir) or placebo control. Data expressed as means±SEM. *P<0.05 vs. Control.
Figure 8D:
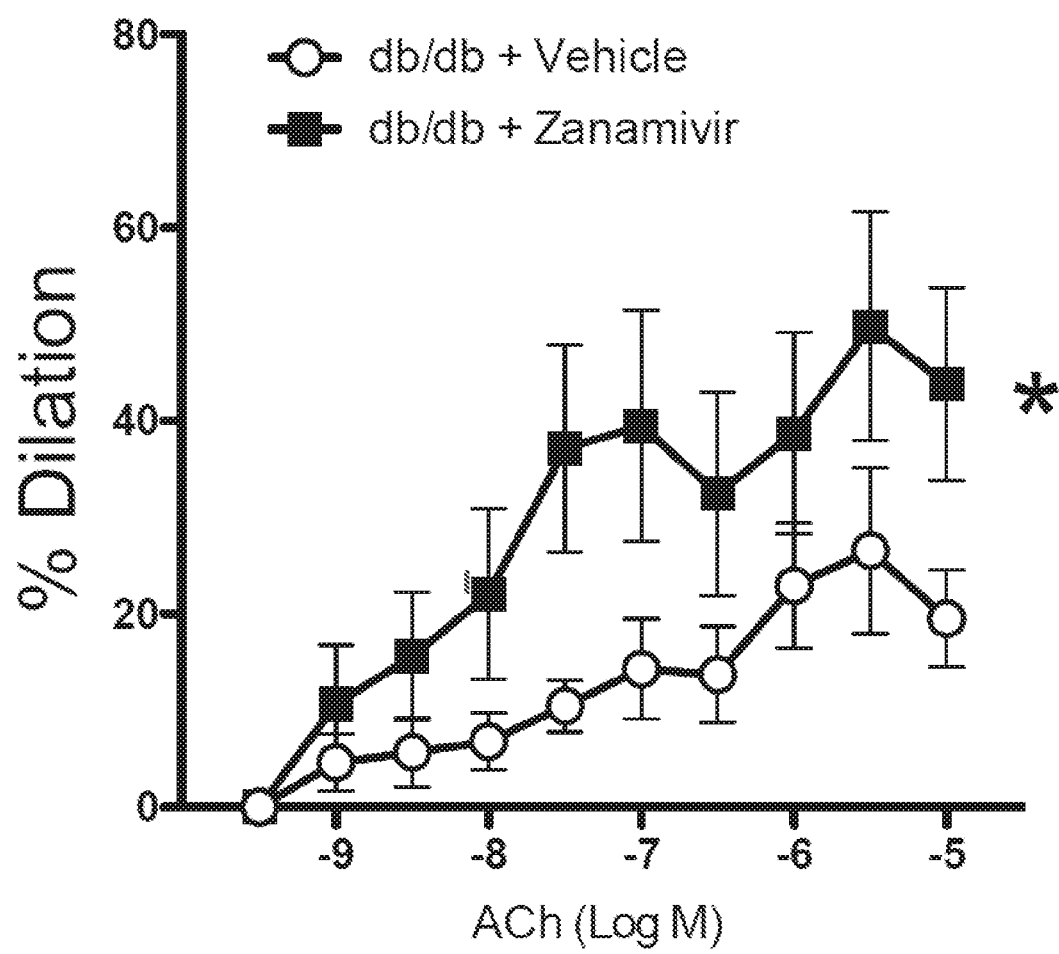
FIG. 8D is a graph depicting improved endothelial dependent vasodilation to acetylcholine in isolated femoral arteries from db/db mice (a mouse model of type 2 diabetes) treated with a neuraminidase inhibitor (Zanamivir) or placebo control. Data expressed as means±SEM. *P<0.05 vs. Control.

In a separate set of experiments, vessels were pre-constricted and exposed to increasing concentrations of insulin (FIG. 8C) or endothelium-dependent vasodilator, acetylcholine (FIG. 8D). The endothelial dependent vasodilatory response of pre-constricted femoral arteries to increasing concentrations of insulin and acetylcholine was greater in Zanamivir treated mice (n=7) versus the vehicle cohort (n=7). Data represent mean+/−SEM, *P<0.05, determined by two-tailed Student t test.

Figure 8E:
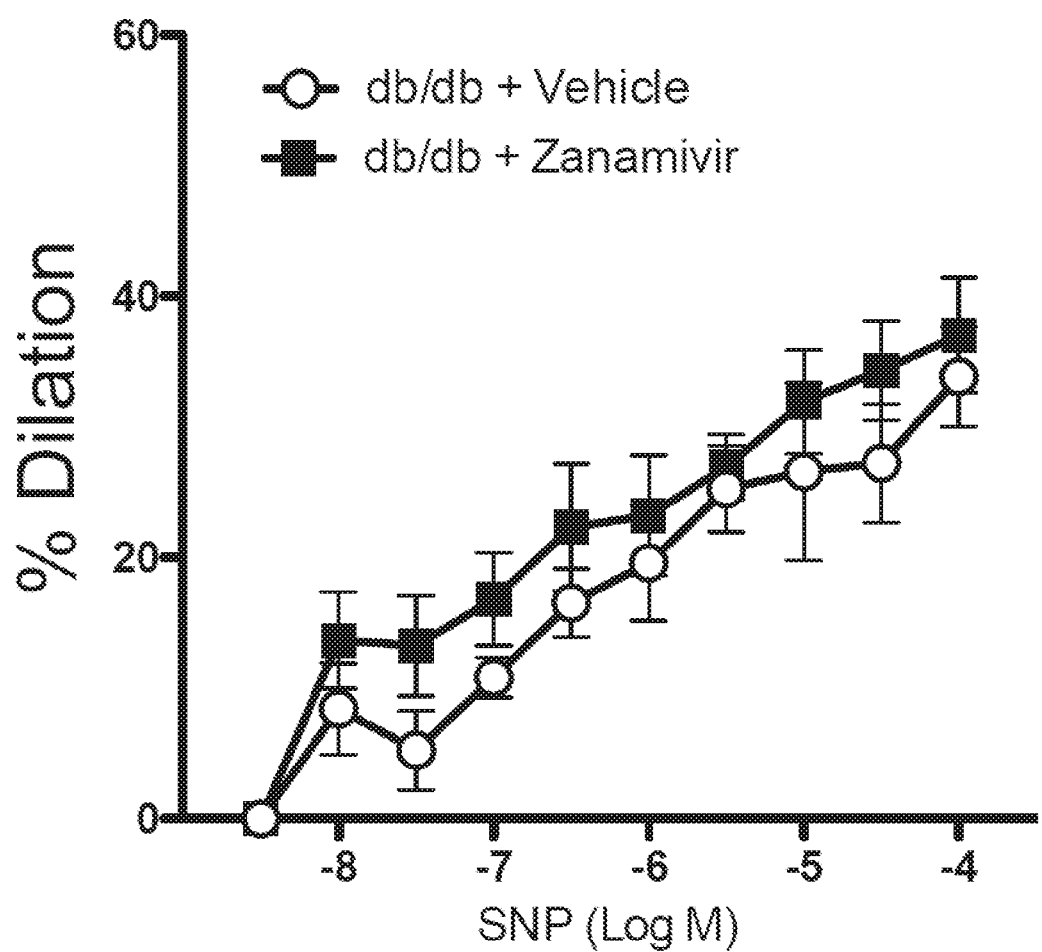
FIG. 8E is a graph depicting vasodilation to sodium nitroprusside in isolated femoral arteries from db/db mice (a mouse model of type 2 diabetes) treated with a neuraminidase inhibitor (Zanamivir) or placebo control. Data expressed as means±SEM.
Figure 8F:
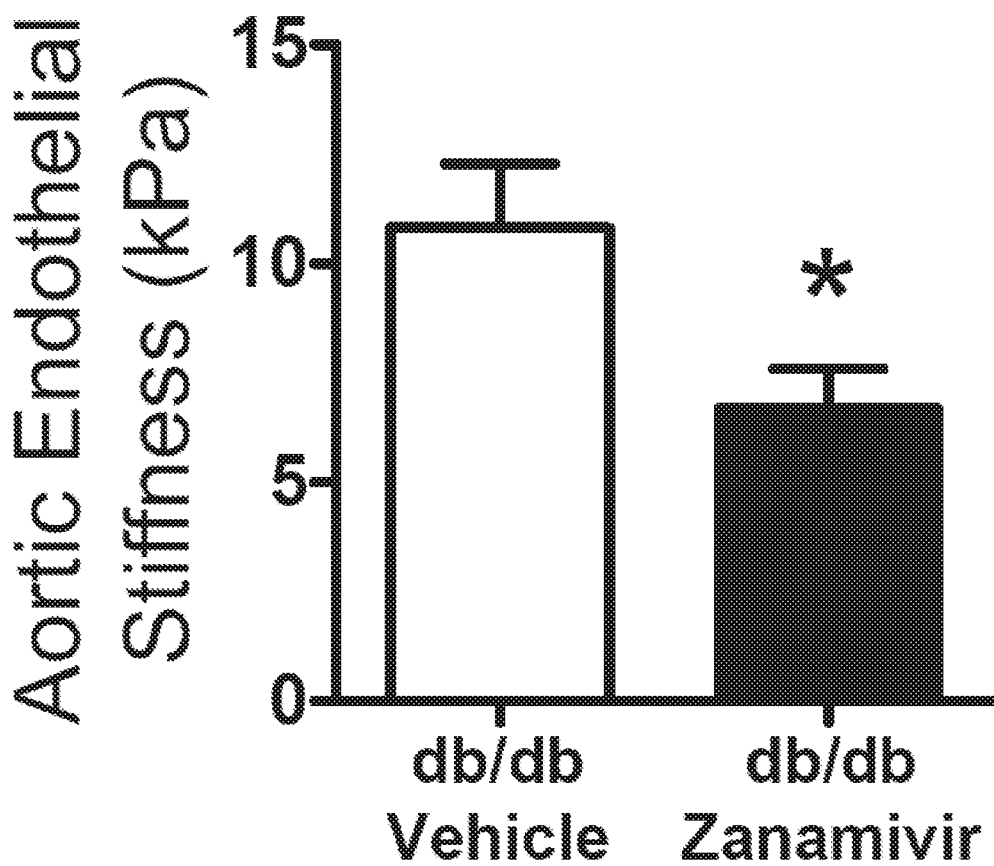
FIG. 8F is a graph depicting atomic force microscopy assessments of aortic endothelial stiffness in isolated Aorta from db/db mice (a mouse model of type 2 diabetes) treated with a neuraminidase inhibitor (Zanamivir) or placebo control. Data expressed as means±SEM. *P<0.05 vs. Control.

FIG. 8E shows that pre-constricted femoral arteries from Zanamivir treated mice (n=6) displayed similar vasodilatory responses to Sodium Nitroprusside (SNP) as vehicle cohort (n=6). Atomic Force Microscopy was used to measure the stiffness of isolated aortas from vehicle (n=8) and Zanamivir treated cohorts (n=8). As depicted in FIG. 8F, there was a significant reduction in aortic endothelial stiffness in the Zanamivir treated cohort. Data represent mean+/−SEM, *P<0.05, determined by two-tailed Student t test.

Example 8

Figure 9:
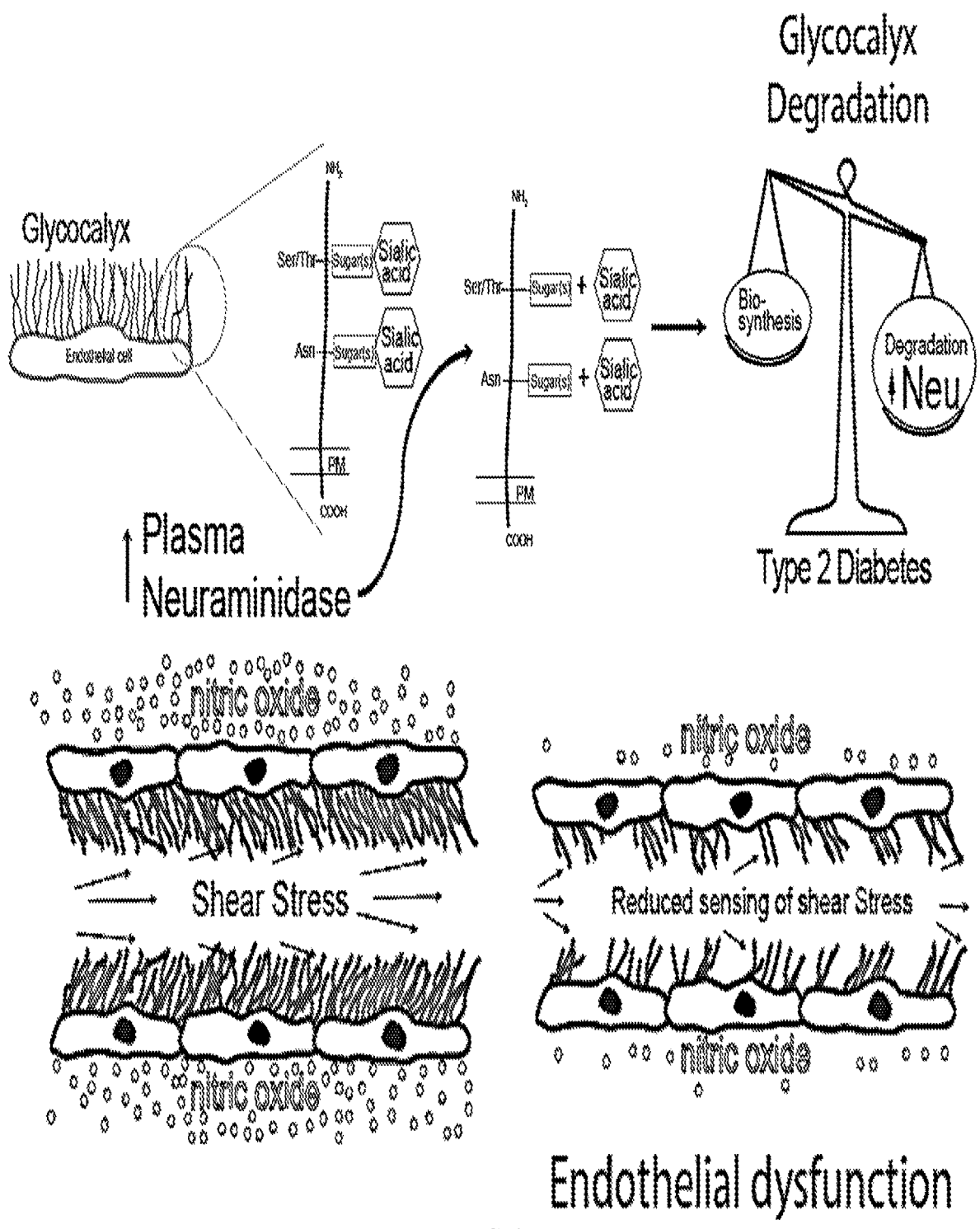
FIG. 9 is a schematic depicting impaired endothelial function in T2D via increased neuraminidase activity that promotes degradation of the glycocalyx and that cleavage of sialic acid residues facilitates shedding of the glycocalyx and reduces the bioavailability of nitric oxide.

As depicted in FIG. 9, the equilibrium of glycocalyx biosynthesis/degradation is shifted towards degradation in type 2 diabetes, due to increased circulating neuraminidase activity. This in turn increases desiallylation of the glycocalyx and facilitates increased shedding of components of the glycocalyx, reducing shear stress mediated nitric oxide production, and thereby impairing FMD in T2D.

What is claimed is:

1. A method for ameliorating glycocalyx damage in an individual in need thereof, the method comprising: administering to the individual in need thereof a composition comprising a neuraminidase inhibitor chosen from Neu5Ac2en ((2R,3R,4S)-3-acetamido-4-hydroxy-2-[(1R,2R)-1,2,3-trihydroxypropyl]-3,4-dihydro-2H-pyran-6-carboxylic acid), a Neu5Ac2en derivative, oseltamivir (ethyl (3R,4R,5S)-5-amino-4-acetamido-3-(pentan-3-yloxy)-cyclohex-1-ene-1-carboxylate), siastatin B ((3S,4S,5R,6R)-6-acetamido-4,5-dihydroxypiperidine-3-carboxylic acid), a siastatin B analog, a siastatin B derivative, and a sialidase.

2. The method of claim 1, wherein the Neu5Ac2en derivative is Zanamivir (5-acetamido-4-guanidino-6-(1,2,3-trihydroxypropyl)-5,6-dihydro-4H-pyran-2-carboxylic acid) and wherein the Zanamivir dosage ranges from about 1 mg/day to about 600 mg/day.

3. The method of claim 1, wherein the individual in need thereof has or is suspected of having diabetes, coronary artery disease, peripheral vascular disease, cerebrovascular disease, atherosclerosis, hypertension, an ischemic disease, a pulmonary disease, an ocular disease, and combinations thereof.

4. The method of claim 1, wherein the individual in need thereof has or is suspected of having type 2 diabetes.

5. A method for treating endothelial dysfunction in an individual in need thereof, the method comprising: administering to the individual in need thereof a composition comprising a neuraminidase inhibitor chosen from Neu5Ac2en ((2R,3R,4S)-3-acetamido-4-hydroxy-2-[(1R,2R)-1,2,3-trihydroxypropyl]-3,4-dihydro-2H-pyran-6-carboxylic acid), a Neu5Ac2en derivative, oseltamivir (ethyl (3R,4R,5S)-5-amino-4-acetamido-3-(pentan-3-yloxy)-cyclohex-1-ene-1-carboxylate), siastatin B ((3S,4S,5R,6R)-6-acetamido-4,5-dihydroxypiperidine-3-carboxylic acid), a siastatin B analog, a siastatin B derivative, and a sialidase.

6. The method of claim 5, wherein the Neu5Ac2en derivative is Zanamivir (5-acetamido-4-guanidino-6-(1,2,3-trihydroxypropyl)-5,6-dihydro-4H-pyran-2-carboxylic acid) and wherein the Zanamivir dosage ranges from about 1 mg/day to about 600 mg/day.

7. The method of claim 5, wherein the individual in need thereof has or is suspected of having diabetes, coronary artery disease, peripheral vascular disease, cerebrovascular disease, atherosclerosis, hypertension, an ischemic disease, a pulmonary disease, an ocular disease, and combinations thereof.

8. The method of claim 5, wherein the individual in need thereof has or is suspected of having type 2 diabetes.

9. A method for improving flow mediated dilation in an individual in need thereof, the method comprising: administering to the individual in need thereof a composition comprising a neuraminidase inhibitor chosen from Neu5Ac2en ((2R,3R,4S)-3-acetamido-4-hydroxy-2-[(1R,2R)-1,2,3-trihydroxypropyl]-3,4-dihydro-2H-pyran-6-carboxylic acid), a Neu5Ac2en derivative, oseltamivir (ethyl (3R,4R,5S)-5-amino-4-acetamido-3-(pentan-3-yloxy)-cyclohex-1-ene-1-carboxylate), siastatin B ((3S,4S,5R,6R)-6-acetamido-4,5-dihydroxypiperidine-3-carboxylic acid), a siastatin B analog, a siastatin B derivative, and a sialidase.

10. The method of claim 9, wherein the Neu5Ac2en derivative is Zanamivir (5-acetamido-4-guanidino-6-(1,2,3-trihydroxypropyl)-5,6-dihydro-4H-pyran-2-carboxylic acid) and wherein the Zanamivir dosage ranges from about 1 mg/day to about 600 mg/day.

11. The method of claim 9, wherein the individual in need thereof has or is suspected of having diabetes.

12. The method of claim 11, wherein the individual in need thereof has or is suspected of having type 2 diabetes.

13. The method of claim 1, wherein the Neu5Ac2en derivative is selected from the group consisting of (2R,3R,4S)-3-acetamido-4-amino-2-[(1R,2R)-1,2,3-trihydroxypropyl]-3,4-dihydro-2H-pyran-6-carboxylic acid, zanamivir (5-acetamido-4-guanidino-6-(1,2,3-trihydroxypropyl)-5,6-dihydro-4H-pyran-2-carboxylic acid), laninamivir ((4S,5R,6R)-5-acetamido-4-carbamimidamido-6-[(1R,2R)-3-hydroxy-2-methoxypropyl]-5,6-dihydro-4H-pyran-2-carboxylic acid), and peramivir ((1S,2S,3R,4R)-3-[(1S)-1-(Acetylamino)-2-ethylbutyl]-4-(carbamimidoylamino)-2-hydroxycyclopentanecarboxylic acid).

14. The method of claim 5, wherein the Neu5Ac2en derivative is selected from the group consisting of (2R,3R,4S)-3-acetamido-4-amino-2-[(1R,2R)-1,2,3-trihydroxypropyl]-3,4-dihydro-2H-pyran-6-carboxylic acid, zanamivir (5-acetamido-4-guanidino-6-(1,2,3-trihydroxypropyl)-5,6-dihydro-4H-pyran-2-carboxylic acid), laninamivir ((4S,5R,6R)-5-acetamido-4-carbamimidamido-6-[(1R,2R)-3-hydroxy-2-methoxypropyl]-5,6-dihydro-4H-pyran-2-carboxylic acid), and peramivir ((1S,2S,3R,4R)-3-[(1S)-1-(Acetylamino)-2-ethylbutyl]-4-(carbamimidoylamino)-2-hydroxycyclopentanecarboxylic acid).

15. The method of claim 9, wherein the Neu5Ac2en derivative is selected from the group consisting of (2R,3R,4S)-3-acetamido-4-amino-2-[(1R,2R)-1,2,3-trihydroxypropyl]-3,4-dihydro-2H-pyran-6-carboxylic acid, zanamivir (5-acetamido-4-guanidino-6-(1,2,3-trihydroxypropyl)-5,6-dihydro-4H-pyran-2-carboxylic acid), laninamivir ((4S,5R,6R)-5-acetamido-4-carbamimidamido-6-[(1R,2R)-3-hydroxy-2-methoxypropyl]-5,6-dihydro-4H-pyran-2-carboxylic acid), and peramivir ((1S,2S,3R,4R)-3-[(1S)-1-(Acetylamino)-2-ethylbutyl]-4-(carbamimidoylamino)-2-hydroxycyclopentanecarboxylic acid).

* * * * *